(12) United States Patent
Booth

(10) Patent No.: US 6,416,489 B1
(45) Date of Patent: Jul. 9, 2002

(54) PROCESS FOR EFFECTING STERILE CONNECTIONS OF MEDICAL TUBING BY WAY OF TERMINALLY STERILIZING AN ISOLATED FLUID FILLED CONNECTED AREA

(76) Inventor: William H Booth, 167 Deer Hollow Rd., Bogart, GA (US) 30622

( * ) Notice: Subject to any disclaimer, the term of this patent is extended or adjusted under 35 U.S.C. 154(b) by 0 days.

(21) Appl. No.: 09/517,274

(22) Filed: Mar. 2, 2000

(51) Int. Cl.[7] .................................................. A61N 1/30
(52) U.S. Cl. ........................................... 604/19; 604/29
(58) Field of Search ........................... 604/19, 29, 408, 604/410, 526

(56) References Cited

U.S. PATENT DOCUMENTS

| | | | |
|---|---|---|---|
| 3,968,195 A | | 7/1976 | Bishop |
| 4,410,026 A | * | 10/1983 | Boggs et al. ............. 137/68.11 |
| 4,610,670 A | * | 9/1986 | Spencer ........................ 604/29 |
| 4,737,214 A | | 4/1988 | Leurink |
| 5,009,654 A | * | 4/1991 | Minshall et al. ............. 604/408 |
| 5,496,302 A | | 3/1996 | Minshall et al. |
| 5,910,138 A | * | 6/1999 | Sperko et al. .............. 604/408 |
| 5,944,709 A | * | 8/1999 | Barney et al. .............. 206/219 |
| 6,083,189 A | * | 7/2000 | Gonon et al. ................ 604/118 |
| 6,165,161 A | * | 12/2000 | York et al. .................. 604/408 |
| 6,023,535 A1 | * | 3/2001 | Barney et al. ................ 53/452 |

* cited by examiner

*Primary Examiner*—Teresa Walberg
*Assistant Examiner*—Vinod Patel

(57) ABSTRACT

A process and apparatus for effecting sterile connections of medical tubing by way of terminally sterilizing an isolated fluid filled connected area with the steps of: isolating the terminal ends of two sealed tubing leads, removing the sealed terminal ends of each tube by cutting off these ends and discarding same, joining the resulting open ends of the respective tube leads together so as to provide a hermetic seal, further isolating a portion of fluid present in one or both of the tube leads, introducing this isolated fluid into the non)-sterile zone created by the opening of the tube ends, exposing the remaining isolated area to sufficient light radiation to sterilize all fluid and surfaces inside the connection area and removing the remaining isolation devices to open a sterile fluid pathway and a system/apparatus for effecting such sterile connections comprising the selection of tubing materials with high ultraviolet light transmission coefficient and with diameter and wall thickness suitable for both light transmission and functional integrity and which may be joined together via heat sealing or mechanical methods, making use of the presence of light transmissive sterile fluid in one or both of the lines (tubes) to be connected by isolating a quantity of this fluid to be transferred to the sterilization zone, and transferring this fluid to the connection zone to be sterilized.

16 Claims, 2 Drawing Sheets

PROCESS FOR EFFECTING STERILE CONNECTIONS OF MEDICAL TUBING BY WAY OF TERMINALLY STERILIZING AN ISOLATED FLUID FILLED CONNECTED AREA

BACKGROUND OF THE INVENTION

Medical products manufacturers and clinicians, including blood collection and storage operators, have frequent need to make a fluid transfer between two or more sterile containers or systems by way of tubing connecting these containers. In the manufacturing environment, it is often necessary to sterilize components or subassemblies of a drug or device by different methods. For example, in a complex product incorporating both a fluid container and a dry set assembly, the solution container may be steam sterilized whereas the set or other components would not be compatible with steam processing. In such a case, the dry components may be terminally sterilized with gas or radiation. The problem arising herewith is how to join these components together as an integrated sterile product when the sterility of the components is compromised in the process of making the connection. In the typical clinical setting, contents from a blood collection container need to be transferred to other sterile containers. Again, the process of making the connection may compromise the sterility of both systems to be connected.

Technologies are currently available and in use in the marketplace to address this need. These technologies may be grouped into three different approaches to the problem of sterility. The first group seeks to maintain the sterility of the connected area through passive means including contamination control measures. A second endeavors to create a sterilizing field or plasma in which the connection is effected. A third approach performs a terminal sterilization on the affected area after the connection is completed. The present invention utilizes this terminal sterilization approach which is considered very reliable with respect to sterility assurance.

Prominent among current technologies is a patented process that incorporates a high voltage (>300 Kev) electron beam to sterilize the connection. In this process (U.S. Pat. No. 5,009,654 and 5,496,302) tubing leading from components sterilized individually by separate methods is clamped near their terminal ends to maintain sterile integrity during the connection process. Each terminal end is cut off, removed, and the ends are then connected together by heat-sealing, solvent bonding, or other methods. Radiation is then applied to the area between the clamps to terminally sterilize and then clamps are removed, opening a sterile pathway. The present invention incorporates some aspects of the above process with additional steps and elements, which serve to create a significant improvement.

The prior technology to which the present invention is most relevant is deficient in its economy. The cost to implement and operate a high voltage electron beam system is high. Special facilities expense is necessary to provide shielding from x-rays and to assure that the possibility for human exposure is minimized. Customized materials handling equipment is required to transport product through the electron beam system. The factory floor space required exceeds that of the present invention.

The present invention addresses these deficiencies in that certain alternate energy sources such as pulsed UV light sterilizing systems operate at faster rates, within a smaller floor space, and at less cost than high voltage electron beams. The system also operates without creating ionizing radiation or other potential work environment hazards. In order to gain these benefits, a new assembly process comprising the steps described in this application is necessary.

FIELD OF THE INVENTION

This invention relates generally to the field of medical drug and device manufacturing, to the field of clinical medical device operations, and more particularly to a process for effecting sterile connections of medical tubing by way of terminally sterilizing an isolated fluid filled connected area.

OBJECT OF THE INVENTION

The primary object of the invention is to provide a sterile connection by terminally treating an isolated connected area after it is resealed.

Another object of the invention is to enable light energy to be employed for terminally sterilizing tubing connections.

Another object of the invention is to provide a more cost effective alternative to methods employing ionizing radiation.

A further object of the invention is to permit implementation of sterile connection technology with less facilities and installation investment than ionizing radiation alternatives.

Yet another object of the invention is to reduce factory floor space requirements from that required by ionizing radiation alternatives.

Still yet another object of the invention is to enable higher levels of microbial inactivation than that provided by other non-ionizing radiation alternative methods such as continuous wave ultraviolet radiation.

Another object of the invention is to take opportune advantage of fluids present in the tubing to be connected.

Another object of the invention is to permit use of a range of olefin polymers for the tubing material.

Other objects and advantages of the present invention will become apparent from the following descriptions, taken in connection with the accompanying drawings, wherein, by way of illustration and example, an embodiment of the present invention is disclosed.

SUMMARY OF THE INVENTION

In accordance with a preferred embodiment of the invention, there is shown a process for effecting sterile connections of medical tubing by way of terminally sterilizing an isolated fluid filled connected area having the steps of isolating the terminal ends of two tubing leads to completely close the respective leads to the passage of contaminants; removing the sealed terminal ends of each tube; joining the resulting open ends of the respective tube leads together so as to provide a hermetic seal and creating a non-sterile zone; further isolating a portion of fluid present in one or both of the tube leads adjacent to said zone; introducing said isolated fluid into said non-sterile zone; exposing the non-sterile zone to means for sterilizing all fluid and surfaces inside said zone; and removing any remaining isolation means to open a sterile fluid pathway.

In accordance with another preferred embodiment, there is shown an apparatus for effecting sterile connections for the flow of biological fluids having two sections of tubing having a high ultraviolet light transmission coefficient, wherein said tubing is joinable and selectively isolatable in sections for exposure of selected sections to sterilization means to create a sterile fluid path in joined tubing.

DETAILED DESCRIPTION OF THE PREFERRED EMBODIMENTS

Figure 1:
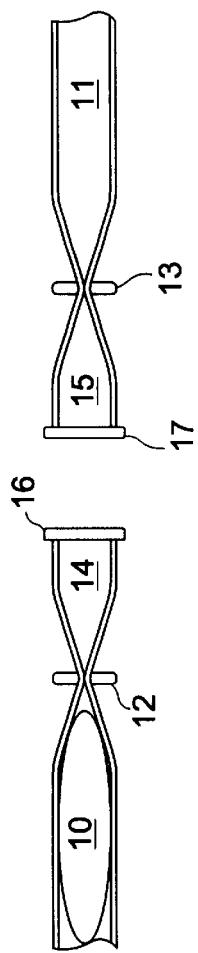
FIG. 1. Cross Sectional View of Clamped Sterile Tubes Prior to Connection Representing the First Process Step.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In the particular method illustrated in FIGS. 1–8, certain steps constitute current practice, represent prior art, and serve as a common starting point for the preferred embodiment. These steps relate to the clamping, cutting, and joining of medical tubing segments. Additionally, the practice of terminally sterilizing the isolated segments of tubing joined in such a manner with a high-voltage electron beam system also constitutes prior art and is currently employed in the industry.

Pursuant to the present invention, provision is made for selection of tubing materials with high coefficient of UV transmission, having diameter and wall thickness to properly function, and for introduction of diluent fluid into the sterilization zone so that alternative energy sources such as pulsed broad spectrum light including particularly the ultraviolet wavelengths may be employed in effecting sterile connections. This light energy is transmitted through the tubing and diluent fluid sterilizing both in a short flash of high intensity.

The sterilization described above is made possible through isolating a volume of clear fluid, either already present in the wet leg of the tube leads to be connected or introduced into one or both of the leads to be connected. Disposable clamps or other mechanical devices, which effectively close off the tubing not permitting the passage of fluids, air, or potential microbial contamination, may provide this isolation. After such isolation is made then the clamp, or other device initially applied to the wet leg tube lead, is released or removed permitting the fluid formerly isolated in this leg to flow into the larger segment of connected tubing defined by the location of the Clamps in FIGS. 4, 5, and 6.

The purpose for this introduction of fluid into the kill zone is to enhance the capacity of certain high intensity pulsed light technology to inactivate microbial spore populations traditionally used to measure the effectiveness of terminal sterilization processes. Challenge organisms in such a diluent suspension may be more vulnerable to inactivation (kill) than challenge organisms inoculated by the drop method upon a dry tubing surface. This assertion has been demonstrated through numerous experiments employing high intensity pulsed light to kill bacterial spores on both dry surfaces and in solution containers (filled bottles). An industry accepted method for inoculating a dry surface to be sterilized is to place a drop of liquid containing approximately 1 million ($1 \times 10^6$) organisms per milliliter on the surface to be treated and allowing this droplet to thoroughly dry. During this dehydrating process, some of the bacterial spores tend to layer upon each other. During the subsequent sterilization, spores on the surface layer absorb more energy than those located under the surface or at lower layers, the topmost spores in effect shadowing others. The result may be incomplete kill of all the organisms present. Studies have shown a reduction of two to six logs of the spore challenge typically may be achieved with high intensity pulsed light systems. The standard method for measuring the sterilizing effects of a process on a filled container differs slightly in that the challenge inoculum is injected into the fluid to be sterilized. It is assumed that the internal container surfaces and the contained solution will be sterilized. When most bacterial spores utilized for sterility validations are injected into a liquid, the spores tend to be more evenly dispersed within the suspension than those in a dried droplet. Typical challenge levels are $1 \times 10^6$ to $1 \times 10^8$ organisms per milliliter of fluid. When exposed to the same sterilizing energy as samples having been drop inoculated, fluid containers typically may yield levels of kill of 6 to 8 logs. It is held that this improved result over drop inoculation is due primarily to the greater degree of dispersion of the challenge bacterial spores in/on the surfaces to be treated. Therefore, the present invention introduces fluid into the segment of tubing to be sterilized for two reasons. First, this segment becomes essentially a fluid container and may then be challenged according to proven and accepted methods for fluid containers. Secondly, if a drop challenge were to be applied to inner tube surfaces to be sterilized, the introduction of fluid to this segment would serve to dilute and further disperse the challenge material so as to reduce and minimize the layering as earlier described.

Additionally, the connection of the tubing to be joined must be performed in such a way as to facilitate light transmission to all interior tubing surfaces. As the light energy must first penetrate the tube wall before it can act upon biological material in the interior spaces, it becomes important to avoid creating areas of high tubing cross sectional thickness, which would absorb the energy. In the present invention, the joining methods employed minimize this "shadowing" effect.

Figure 2:
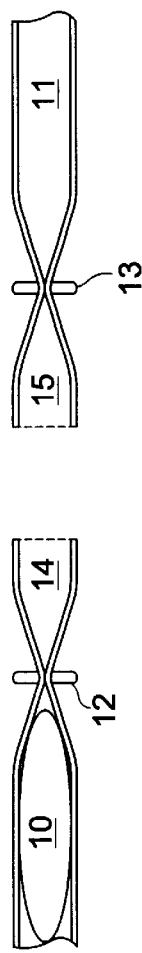
FIG. 2. Cross Sectional View of Tubes Prior to Joining Representing the Second Process Step.
Figure 3:
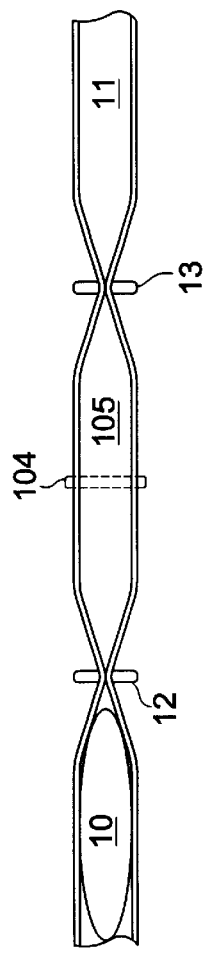
FIG. 3. Cross Sectional View of Joined Tubing Representing the Third Process Step.
Figure 4:
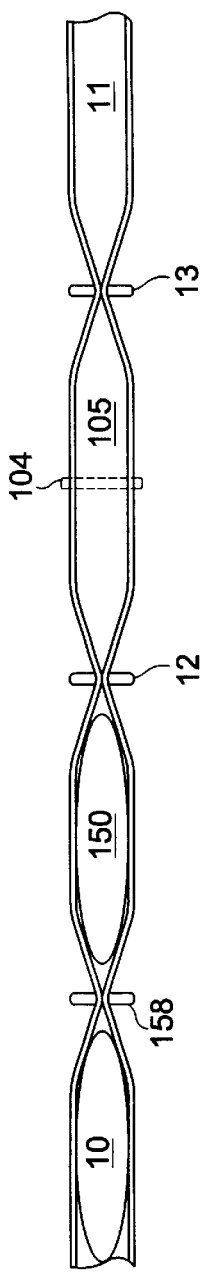
FIG. 4. Cross Sectional View of Isolated Diluent in the Tubing Representing the Fourth Process Step.
Figure 5:
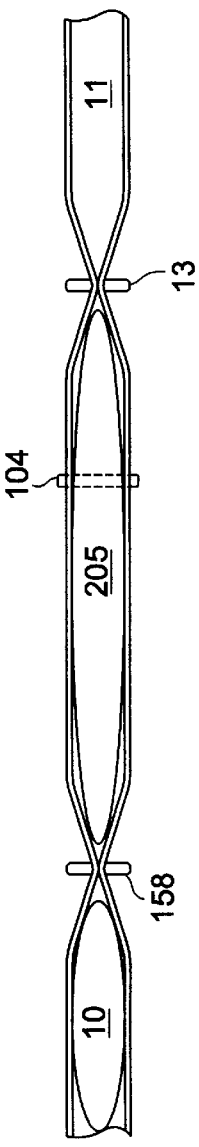
FIG. 5. Cross Sectional View of Non-sterile Zone of Connected Tubing Prior to Sterilization Representing the Fifth Process Step.
Figure 6:
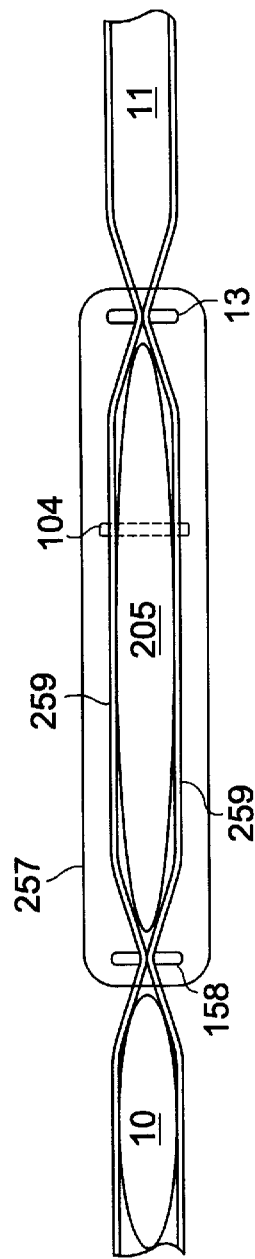
FIG. 6. Cross Sectional View of Non-sterile Zone Illustrating Sterilization Treatment Area Representing the Sixth Process Step.
Figure 7:
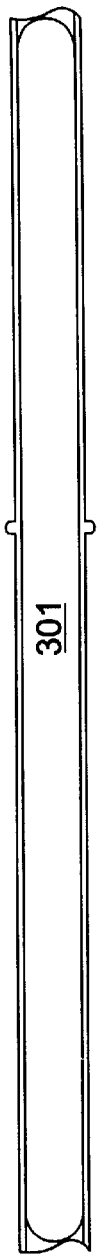
FIG. 7. Cross Sectional View of Open Sterile Pathway Illustrating Completed Sterile Connection and Representing the Final Process Step.

In operation, the essential steps comprising the process will be as follows: Turning first to FIG. 1, the tubes leading from the sterile systems to be joined are clamped with medical grade plastic slide clamps (12, 13) or facsimile at a point approximately 1 or more inches from the sealed terminal ends (16, 17) of the respective tubes (14, 15). Turning to FIG. 2., the tube ends from both leads are cut away and discarded leaving open sections of tubing (14, 15). Next, in FIG. 3., tube ends are joined together by way of heat sealing (104) or other means creating a non-sterile connection zone (105). In FIG. 4. It is illustrated that a third clamp of the type used in the FIG. 1 is applied to the "wet" line at a point upstream of the original clamp on this line (158). The distance from the third clamp (158) to the original clamp on the line (12) may be varied to control the quantity of diluent (150) introduced into segment to be sterilized (205). The original clamp on the "wet" line (12) is then removed or otherwise released. Referring to FIG. 5., the prior step permits fluid from the segment isolated by the third clamp (150) to flow into the non-sterile segment (205). Mechanical assistance may be applied in transferring this fluid into the non-sterile segment. Finally, the segment or area then isolated by the remaining two clamps (205) is sterilized by means of non-ionizing radiation applied from outside the tube. As illustrated in FIG. 6., pulsed broad-spectrum light will penetrate the tube walls (259) and solution isolated by the clamps (158, 13) inactivating a minimum of 6 logs of microbial challenge in the region defined by the treatment zone (257). Referring to FIG. 7., the clamps (158, 13 from FIG. 6.) are removed or otherwise opened creating a sterile path for the fluids (301) to be transferred between systems.

Figure 8:
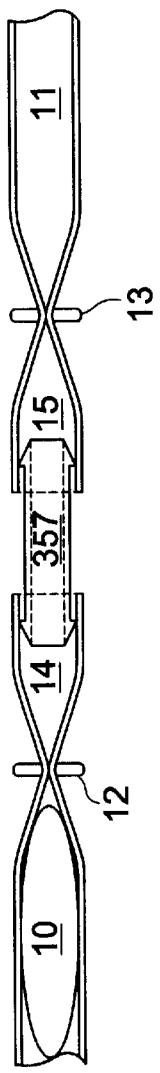
FIG. 8. Illustration of Alternate Embodiments of Joining Methods.

Alternate methods of connecting the tubing may include those depicted in FIG. 8 wherein a light transmissive plastic sleeve (351) is sealed by heat or other means to the tube ends (14, 15) or a mechanical connector (357) may also be employed provided UV light transmission and functional requirements are satisfied.

The advantages of this process include the speed with which sterilization may be effected versus existing electron beam systems and the reduced cost of implementing a pulsed light sterilization system versus a high voltage electron beam system.

High intensity pulsed light sterilization systems employ advanced electrical capacitor and switching technology to generate and deliver very short, high voltage bursts of electricity to an inert gas filled tube housed within a flash assembly. This flash is directed toward the product to be treated with light waves of various spectra penetrating light transmissive materials in the product. Bacteria absorbing this energy are inactivated. The present invention makes no claim to the technology of pulsed light sterilization per se.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A process for effecting sterile connections of medical tubing by way of terminally sterilizing an isolated fluid filled connected area comprising the steps of:

a. Isolating the terminal ends of two tubing leads to completely close the respective leads;
   b. Removing the sealed terminal ends of each tube;
   C. Joining the resulting open ends of the respective tube leads together so as to provide a hermetic seal and creating a non-sterile zone;
   d. Further isolating a portion of fluid present in one or both of the tube leads adjacent to said zone;
   e. Introducing said isolated fluid into said non-sterile zone;
   f. Exposing the non-sterile zone to means for sterilizing all fluid and surfaces inside said zone; and
   g. Removing any remaining isolation means to open a sterile fluid pathway.

2. A process as claimed in claim 1 wherein said isolation is by pinching the tubing.

3. A process as claimed in claim 1 wherein said isolation is by clamping the tubing.

4. A process as claimed in claim 1 wherein said tubing leads are sealed at their ends.

5. A process as claimed in claim 1 wherein said joining is by heatseal butt-welding.

6. A process as claimed in claim 1 wherein said joining is by a connector.

7. A process as claimed in claim 6 wherein said connector is a barbed-ended tube.

8. A process as claimed in claim 6 wherein said connector is a generally cylindrical sleeve.

9. A process as claimed in claim 1 wherein said sterilization is by high intensity pulsed light radiation.

10. A process as claimed in claim 1 further comprising the step of contacting substantially all surfaces of the non-sterile zone with the sterilized fluid.

11. A process as claimed in claim 1 wherein said contaminants may be liquid, air, or microbial.

12. An apparatus for effecting sterile connections for the flow of drug and biological fluids comprising:

Two sections of tubing having a high ultraviolet light transmission coefficient, wherein said tubing is joinable and selectively isolatable in sections for exposure of selected sections to sterilization means to create a sterile fluid path in joined tubing.

13. An apparatus as claimed in claim 12 wherein said isolation is by pinching the tubing.

14. An apparatus as claimed in claim 12 wherein said isolation is by clamping the tubing.

15. An apparatus as claimed in claim 12 wherein said joining is by heat seal welding.

16. An apparatus as claimed in claim 12 wherein said sterilization means is by high intensity pulsed light radiation.

* * * * *